(12) United States Patent  
Olsson et al.

(10) Patent No.: US 8,395,661 B1  
(45) Date of Patent: Mar. 12, 2013

(54) PIPE INSPECTION SYSTEM WITH SELECTIVE IMAGE CAPTURE

(75) Inventors: Mark S. Olsson, La Jolla, CA (US); Michael J. Martin, San Diego, CA (US); Ray Merewether, La Jolla, CA (US); Stephen M. Bench, Carlsbad, CA (US); Tran Nguyen, San Diego, CA (US)

(73) Assignee: SeekTech, Inc., San Diego, CA (US)

( * ) Notice: Subject to any disclaimer, the term of this patent is extended or adjusted under 35 U.S.C. 154(b) by 878 days.

(21) Appl. No.: 12/399,859

(22) Filed: Mar. 6, 2009

Related U.S. Application Data

(60) Provisional application No. 61/152,947, filed on Feb. 16, 2009.

(51) Int. Cl.  
*A61B 1/06* (2006.01)

(52) U.S. Cl. .................. 348/86; 348/207.99; 348/61

(58) Field of Classification Search .............. 348/84, 348/207.99, 61  
See application file for complete search history.

(56) References Cited

U.S. PATENT DOCUMENTS

| | | | | |
|---|---|---|---|---|
| 4,558,413 A | * | 12/1985 | Schmidt et al. | 717/170 |
| 6,381,742 B2 | * | 4/2002 | Forbes et al. | 717/176 |
| 7,761,948 B2 | * | 7/2010 | Irwin | 15/104.095 |
| 2005/0275725 A1 | * | 12/2005 | Olsson et al. | 348/207.99 |
| 2010/0225752 A1 | * | 9/2010 | Bench et al. | 348/61 |

* cited by examiner

*Primary Examiner* — Tammy Nguyen  
(74) *Attorney, Agent, or Firm* — Steven C. Tietsworth

(57) ABSTRACT

Various pipe inspection systems include a camera head operatively connected to the distal end of a push-cable. Images may be automatically captured at predetermined distances of travel, or may be automatically captured based on the output signals from the auto-focus, auto-exposure and/or auto-white balance engines indicating, for example, that the camera motion within the pipe is substantially zero. Images may be captured in an automatic mode at predetermined intervals as the camera head travels within the pipe or in an override mode initiated by operator command. The system may include a data transmission circuit that transmits data between a plurality of nodes at a frequency that does not substantially interfere with a normal base band video transmission frequency.

28 Claims, 10 Drawing Sheets

PIPE INSPECTION SYSTEM WITH SELECTIVE IMAGE CAPTURE

PRIORITY CLAIM

This application claims the filing date of U.S. Patent Application Ser. No. 61/034,907 filed Mar. 7, 2008, naming Mark S. Olsson et al. as co-inventors and entitled "Pipe Inspection Imaging System." The entire disclosure of the aforementioned provisional patent application is hereby incorporated by reference.

CROSS-REFERENCE TO RELATED APPLICATIONS AND PATENT

This application is related to U.S. patent application Ser. No. 11/928,818 filed Oct. 30, 2007, naming Mark S. Olsson and David A. Cox as co-inventors and entitled "Pipe Mapping System." It is also related to U.S. Pat. No. 6,908,310 entitled "Slip Ring Assembly with Integral Position Encoder," granted Jun. 21, 2005, to Mark S. Olsson, et al. It is also related to U.S. patent application Ser. No. 12/371,540 filed on Feb. 13, 2009 by Mark S. Olsson et al entitled "High-Performance Push-cable" and U.S. patent application Ser. No. 61/152,947 filed on Feb. 16, 2009, naming Mark S. Olsson, et al, as inventors and entitled "Pipe Inspection System with Replaceable Cable Storage Drum." The entire disclosures of the aforementioned applications and patent are hereby incorporated by reference.

BACKGROUND

1. Field of the Invention

This invention relates generally to electronic and mechanical systems and methods for inspecting the interior of pipes and other conduits and more specifically to a pipe inspection system employing a camera head connected to the end of a push-cable.

2. Description of the Related Art

There are many situations where it is desirable to internally inspect long lengths of pipe that are already in place, either underground, in a building, or underwater. For example, sewer and drain pipes frequently must be internally inspected to diagnose any existing problems and to determine if there are any breaks causing leakage or obstructions impairing the free flow of waste. It is also important to internally inspect steam pipes, heat exchanger pipes, water pipes, gas pipes, electrical conduits, and fiber optic conduits for similar reasons. Frequently, pipes that are to be internally inspected have an internal diameter of six inches or less, and these pipes may make sharp turns. It is sometimes necessary to internally inspect several hundred feet of pipe.

Video pipe inspection systems have been developed that include a video camera head that is forced down the pipe to display the pipe interior on a video display. The inspection is commonly recorded using a video recorder (VCR) or digital video disk (DVD). Conventional video pipe inspection systems have included a semi-rigid push-cable that provides an electromechanical connection between the ruggedized camera head that encloses and protects the video camera and a rotatable push reel used to pay out cable and force the camera head down the pipe. The video push-cable must be specially designed to be flexible enough to make tight turns yet rigid enough to be pushed hundreds of feet down small diameter pipe. The video push-cable needs to incorporate electrically conductive cable having the proper conductors and impedance for conveying the NTSC or other video signals to the video display unit and for coupling to external power and ground conductors. Examples of suitable video push-cables are disclosed in U.S. Pat. No. 5,457,288 issued Oct. 10, 1995 to Mark S. Olsson and U.S. Pat. No. 5,808,239 issued Sep. 15, 1998 to Mark S. Olsson. The video camera head design and the manner in which it is connected to the distal end of the video push-cable are important to the performance and reliability of a video pipe inspection system. These structures must be rugged, yet the camera head must be compact and its manner of connection to the video push-cable flexible enough to bend through tight turns.

A conventional video pipe inspection system includes a reel inside which the video push-cable is wound for storage. The reel is supported on a frame for rotation about a horizontal or a vertical axis for paying out the video push-cable and for rewinding the video push-cable for storage. A slip ring assembly is typically included in the hub and/or axle of the reel to continue electrical connections between the proximal end of the video push-cable and external circuits that power the video camera head and receive video signals therefrom.

Conventional video pipe inspection systems provide the operator little more than direct video-image information, sometimes time-tagged by frame in the recording. Most conventional video pipe inspection systems provide a disoriented video image whenever the camera head rotates away from alignment with the longitudinal axis of the pipe being inspected because of such issues as uncontrolled push-cable torque or navigation through a bend or joint in the pipe. Video images from conventional video pipe inspection systems are usually provided with a single uniform (typically only moderate) resolution. Conventional video pipe inspection systems typically record images at the normal rate of the DVD or VHS recorder, or record none at all. Some conventional video pipe inspection systems allow individual still shots to be taken when the operator issues a button-press or similar command pulse to the unit.

SUMMARY OF THE INVENTION

It would, therefore, be desirable to provide a pipe inspection system with enhanced imaging capabilities and improved communication between the camera head and the external electronics associated with the reel.

In accordance with an embodiment of the present invention, a pipe inspection imaging system includes a push-cable and a camera head operatively connected to a distal end of the push-cable. The camera head includes an image sensor capable of generating images of an interior of a pipe in which the camera head is inserted. Processing circuitry is connected to the image sensor and is configured to enable images to be automatically captured at predetermined distances traveled by the camera head within the pipe.

DETAILED DESCRIPTION

Figure 1:
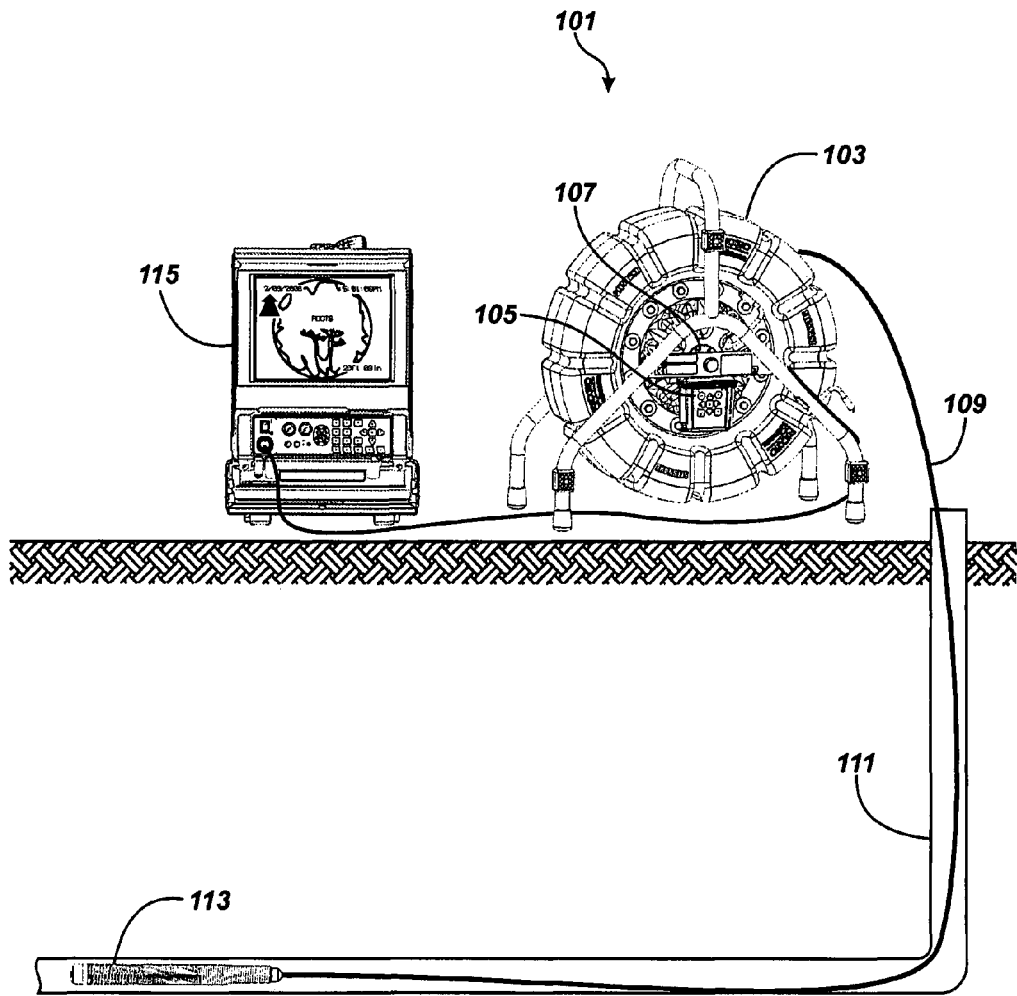
FIG. 1 is a diagrammatic illustration of an exemplary embodiment of the pipe mapping system of the present invention.

In one embodiment the present invention provides a pipe inspection system that automatically captures images at user-defined increments of distance traveled down the pipe, as well as display overlays. The overlays can indicate the current distance measurement and direction of travel (downward or upward) of the camera head in the pipe being inspected. It additionally provides advantages in managing images, adding comments and date stamps to images, and storing images to removable media at user discretion.

The present invention also provides a pipe inspection system that allows for storage of images in a readily removable portable storage device. The storage device can be used to transfer images showing their measured distance or location to a portable printer for immediate inclusion in an inspection debrief or report, using a conventional portable computer. Electronic transfer through wireless, USB cable, Fire-wire or other means may be used.

In another embodiment of the present invention a pipe inspection system is provided that transmits images along wiring embedded in a push-cable with improved fidelity of the displayed images despite variable cable length and differing temperatures inside the pipe.

In another embodiment of the present invention, a pipe inspection system includes a camera head having an image sensor and one or more local condition sensors, each producing a corresponding sensor data signal; a semi-rigid resilient flexible push-cable coupled to the camera head for urging the camera head along the interior of the pipe under test; a processor for producing a GUI image data signal representing conditions in the pipe under inspection responsive to a local condition sensor data signal; a cable measurement system capable of measuring and digitally reporting distance traveled by the camera head moving through the pipe and the direction of its movement; and a display coupled to the processor for displaying to an operator, at a predetermined resolution, a GUI image responsive to the GUI image signal and incorporating user-selected digital overlays of the image representing pipe distance, movement direction, or other displayed information.

In another embodiment, a video pipe inspection system for capturing incremental images from a pipe under inspection includes a camera head having an image sensor with a field of view (FOV) and an output that provides an image-sensor data signal representing a FOV image. A semi-rigid resilient flexible push-cable is coupled to the camera head for urging the camera head along the interior of the pipe under inspection. A processor executes a program that creates digital overlays based on measurement data, and produces a composite camera image with overlaid digital display representing camera distance, direction of camera movement and other information, and stores such composite images to local storage device for use in other reporting systems. The system can translate magnetically signaled rotary motion of the cable drum into distance information and directional information for incorporation into a digital display, while compensating for variables such as cable length, ambient temperature and the like and their impact on the quality of transmitted images. A user interface allows the user to define distance increments at which images will be automatically captured and stored. The system can incorporate one or more image storage devices such as, for example, an SD card, memory stick, USB thumb drive, or similar device enabling the capture and storage of such images with or without operator activation, and may initiate capture to a portable storage device automatically if a target device is present in the system during an inspection. The user interface can be linked to a standard portable keyboard, and that allows the user to title and store selected frames from the video feed with overlaid text lines of titling or comments. Where the camera head includes a video camera, separate image frames may be saved as separate files on a portable storage medium such as an SD Card, a USB thumb drive, both, or some other removable media.

The present invention also provides a pipe inspection system that includes a data link that improves image fidelity in operation. The data link may be added "on top of" (at a frequency that does not interfere with) the existing video signals, using the same conductors in the push-cable. This keeps the number of conductors in the push-cable to a minimum making the push-cable more flexible and automatically compensating for degradation in the video signal going through the push-cable.

In another embodiment of the present invention, electronic data from the chip set of the camera in the camera head is used to detect the state of motion or rest of the camera head and used to determine points in time at which images of the pipe interior should be captured, using a suitable algorithm. Additionally, automatic recognition of side-branch connections in a pipe can be enabled through this improvement.

In still another embodiment of the present invention, processing circuitry is connected to the image sensor in the camera head and is configured to enable images to be captured in an automatic mode at predetermined intervals as the camera head travels within the pipe or in an override mode initiated by operator command.

Another embodiment of the present invention automatically captures the most succinct set of images during a pipe inspection in order to maximize the information content and minimize the size of the stored inspection files. While the camera head is moving (being urged forward within the pipe by the operator), images captured during this movement (forward or backwards displacement along the inside of the pipe) are motion-blurred and are generally not useful for inspection purposes per se. However, these blurred images have some value and purpose in that they provide continuity during playback and give the observer a sense of relative position and orientation of the camera head within the pipe. These images may optionally be combined with a sound track, and help make the story of the pipe inspection more coherent and meaningful to a later observer viewing the playback. On the other hand, when the camera is stopped nothing important to the operator or inspector is changing and a single captured high resolution still image is preferably generated in order to record details the condition of that location within the pipe being inspected. Therefore, an embodiment of the present invention can provide a relatively small number of relatively high resolution (larger file size) images each time the camera head stops or pauses within the pipe and then a series of time or distance (or some combination thereof) spaced, relatively low resolution (smaller file size) images while the camera head is moving and the images are motion blurred. Thus this embodiment includes processing circuitry connected to the image sensor and configured to enable images of the interior of the pipe to be automatically captured at different resolutions depending on an optically detected state of motion of the camera head within the pipe.

The drum rotation counter can accurately indicate the distance of penetration of the camera head into the piping system and over time scales of several seconds and this distance information provides a reliable indication of when the operator is actively moving the camera. However, there is a certain amount of cable slack between the rotation of the drum and the actual instantaneous movement of the camera head within the pipe. The drum rotation counter is often slightly out of phase in time with camera head motion and therefore with the motion-blurred images. A direct, image based indication of camera motion avoids capturing motion-blurred high resolution images. Such an indication may be derived from the change in the actual camera signal.

Another embodiment of the present invention is a pipe inspection system that utilizes variable frame rate motion jpeg video to create a digital pseudo-video file that is substantially smaller than a conventional digital video file. There are many instances where an operator would like to store a pipe inspection on a portable memory device, such as a memory card, or to transmit the results of the pipe inspection over the Internet. If the digital video is too large it may be impractical to store the same on a portable memory device and/or to transmit the file to a customer over the Internet. The pipe inspection typically consists of a visible portion and an audio portion. As the camera head is pushed down the pipe, there are times when the push-cable is being manually advanced and the camera head is moving forward within the pipe. At other times the camera head is stationary. During the inspection there will often be an audio overlay wherein the operator is describing what is visible at that particular instant, the location of the camera head, and assessing any obstructions, etc. When the camera head is stationary, the view of the pipe is not changing because the camera head is stationary, yet if a conventional MPEG video file were generated the same identical image of the interior of the pipe would be generated by the camera and stored over and over. This creates an unnecessarily large digital video file. Variable frame rate motion jpeg video is used in an embodiment of the present invention to automatically capture a first larger set of images when the camera head is moving within the pipe and a substantially smaller second set of images when motion of the camera head has stopped. The motion of the camera can be detected via accelerometer or other sensor output, or optically using the auto-focus engine, for example. A pseudo-video file can be generated utilizing variable frame rate motion jpeg processing so that when stored and later viewed the pseudo-video file appears to display the interior of the pipe in real time as the camera head moves within the pipe, with images in the second set being re-played to fill in the time when the camera head is not moving, instead of storing multiple identical images. This use of variable frame rate motion jpeg algorithms substantially reduces the size of the pseudo-video file compared to a conventional MPEG file. The images in the first set could have a lower resolution and the images in the second set could have a higher resolution, although this is not necessary to achieve the advantages of this embodiment. The audio portion of the pipe inspection can be synchronized with the video portion of the pseudo-video file. When the pseudo-video file is viewed the fact that the same digital frames taken during stoppage of motion of the camera head are replayed over and over is transparent to the user. In other words, when viewed the digital pseudo-video file appears to the viewer to be identical to a digital video file generated in a conventional manner.

The improvements described herein may be implemented in a video pipe-inspection system embodiment of the type disclosed in U.S. Pat. No. 6,545,704, entitled "Video Pipe Inspection Distance Measuring System," granted Apr. 18, 2003, to Mark S. Olsson et al., the entire disclosure of which is hereby incorporated by reference.

The entire disclosure of U.S. patent application Ser. No. 11/928,818, filed Oct. 30, 2007, of Mark S. Olsson et al., entitled "Pipe Mapping System" is also incorporated herein by reference.

Referring to FIG. 1, a pipe inspection system 101 includes a camera head 113 operatively connected to the distal end of a push-cable 109. The proximal end of the push-cable 109 is operatively connected to a cable-counter and user interface panel 105 through a slip-ring assembly. Examples of suitable constructions for the camera head 113 are disclosed in U.S. Pat. No. 6,831,679 entitled "Video Camera Head with Thermal Feedback Control," granted to Mark S. Olsson et al. on Dec. 14, 2004, and in U.S. patent application Ser. No. 10/858,628 entitled "Self-Leveling Camera Head," of Mark S. Olsson filed Jun. 1, 2004, the entire disclosures of which are hereby incorporated by reference. Push-cable constructions and termination assemblies suitable for use in connecting the proximal and distal ends of a push-cable are disclosed in U.S. Pat. No. 5,939,679 entitled "Video Push Cable" granted Aug. 17, 1999 to Mark S. Olsson, U.S. Pat. No. 6,958,767 entitled "Video Pipe Inspection System Employing Non-Rotating Cable" granted Oct. 25, 2005, to Mark S. Olsson et al., U.S. patent application Ser. No. 12/371,540 filed Feb. 13, 2009 entitled "Push-Cable for Pipe Inspection System," and U.S. Patent Application Ser. No. 61/152,947 filed Feb. 16, 2009 by Mark S, Olsson et al. entitled "Pipe Inspection System with Replaceable Cable Storage Drum," the entire disclosures of which are hereby incorporated by reference. In FIG. 1, a reel 103 holds coils of the push-cable 109. The push-cable 109 is paid out from reel 103 to force camera head 113 down pipe 111. Examples of a suitable reel 103 and push-cable 109 are disclosed in the aforementioned U.S. Pat. No. 6,958,767. Within the reel 103, a slip-ring assembly 107 provides rotary signals to an associated circuit board (not shown) which enables them to be translated into digital measurements of distance traversed by the push-cable 109 based on the rotation of the drum. One example of a suitable slip ring assembly is disclosed in U.S. Pat. No. 6,908,310 entitled "Slip Ring Assembly with Integral Position Encoder," granted Jun. 21, 2005, to Mark S. Olsson et al., the entire disclosure of which is hereby incorporated by reference. The camera head 113 with its on-board circuitry transmits image information through embedded conductors such as wires in the push-cable 109. A display unit 115 shows the updated field of view (FOV) image from the camera head 113 with an overlay indicating the distance down-pipe and the direction of travel based on the values transmitted from the slip ring assembly 107. Circuit boards within the user-interface assembly 105 provide memory and processing, user information display and input controls.

Figure 2:
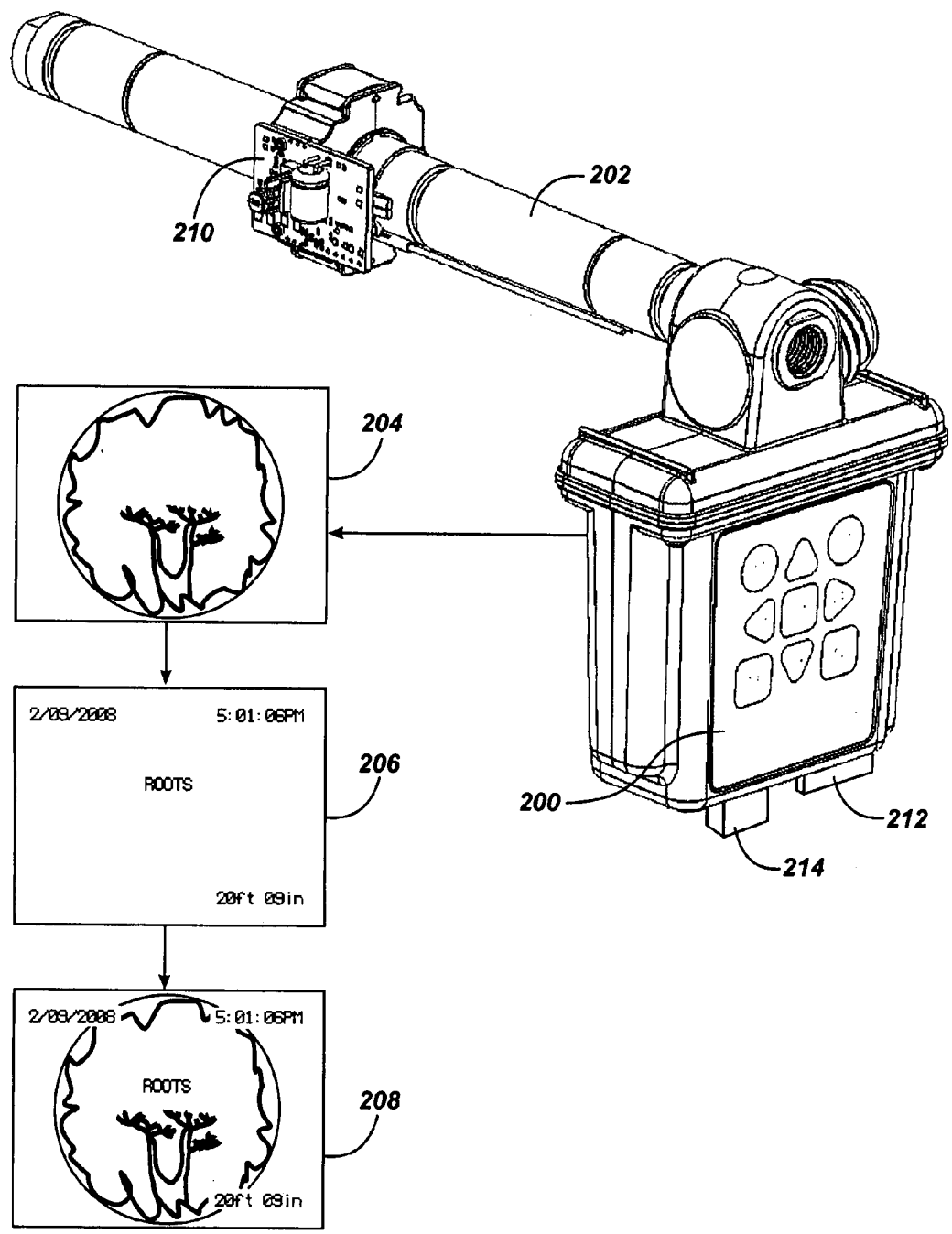
FIG. 2 is a part isometric, part diagrammatic view illustrating details of the system of FIG. 1 including its shaft/slip-ring combination, user-interface keypad, portable storage devices, and video image overlay keypad.

Turning now to FIG. 2, a shaft and slip-ring assembly 202 provides rotary impulses representing distance information to a circuit board 210 which are digitally converted and transmitted to the processing component (not illustrated in FIG. 2) within the user-interface assembly 200. Programmed capabilities within the user-interface unit 200 capture video images such as 204 from the camera head 113 and combine them with distance and direction information into an overlay such as 206, forming a composite image 208 containing both image and distance/direction information which is time-tagged and stored to SD card 212. Direction information is obtained from accelerometers, magnetic sensors, tilt sensors or other sensors in the camera head 113. Under program control, the images may also be automatically written to an alternate removable medium storage shown as a USB thumb drive 214. The UI assembly 200 also includes a keypad and an optional portable printer (not illustrated). User-defined titling, comments, and tags may be added to one or any of the images associated with a given inspection cycle via the keypad, and the composite images 208 thus created may be stored to the SD card 212 or the thumb-drive 214, and printed for delivery to the site owner/customer via printer (not illustrated).

Figure 3:
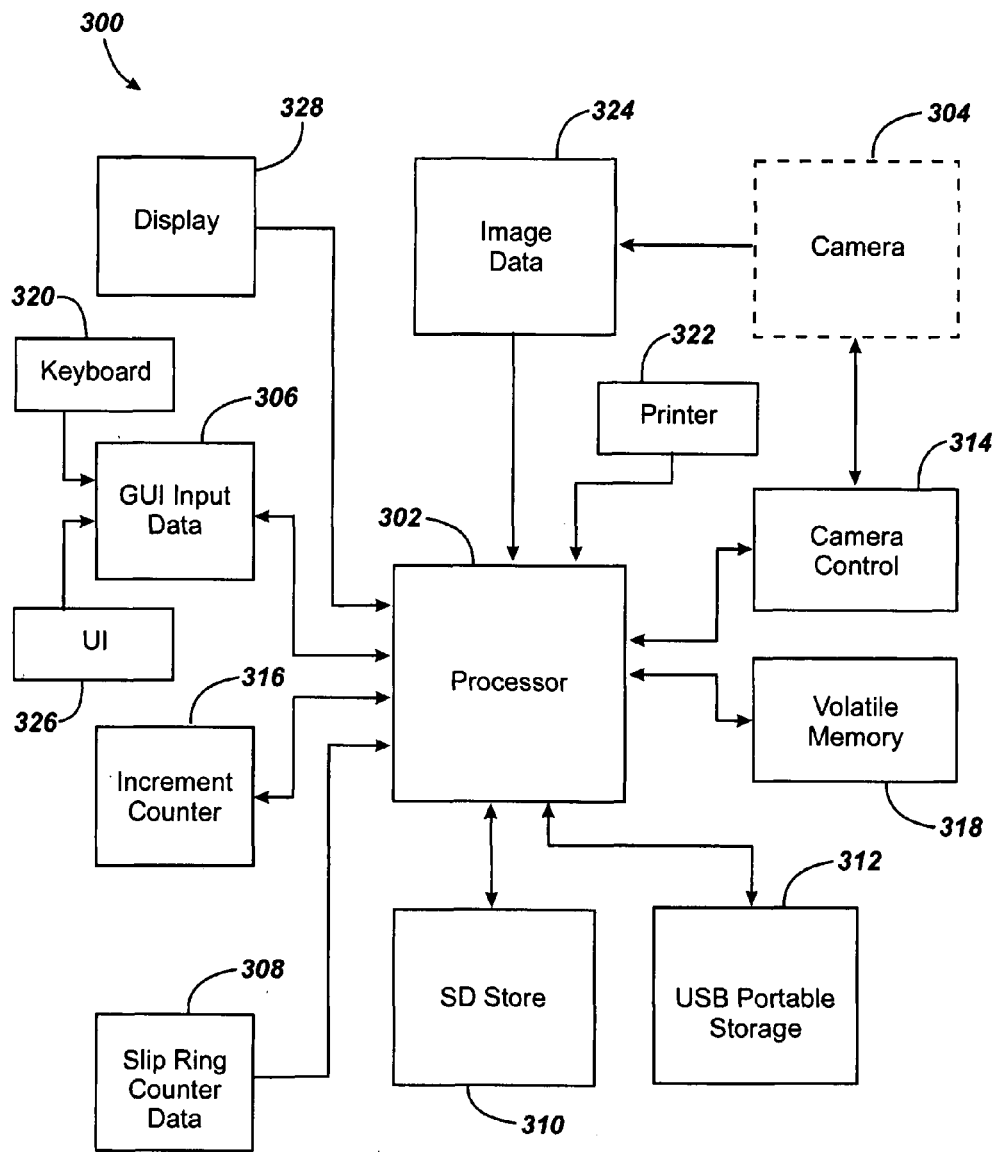
FIG. 3 is a block diagram illustrating the electronic portion of the system of FIG. 1 that processes the flow of image data, camera control data, distance counter data, user interface data, and display information.

Turning now to FIG. 3, the electronic portion 30 of the pipe inspection system 101 includes a central processor 302 associated with a volatile memory 318, which receives input data from a user interface 306, a slip-ring counter 308, a camera head 304 providing image data 324, camera control circuitry 314, a system user interface 326, and a keyboard 320. The central processor 302 sends output signals to the display 328, camera control 314, volatile memory 318, SD card storage 310, USB portable (thumb drive) storage 312, and the user interface 326 with its associated display 328. The transfer of image and other data may be automated through firmware programming or initiated from the GUI 326 using on-board key presses, or by means of the keyboard 320. Algorithmic options in the firmware may permit parameters such as distance-interval between image captures, for example, to be set to default values in automatic operation or to be set to user selected values using menu options exercised through UI 326 or keyboard 320.

Figure 4:
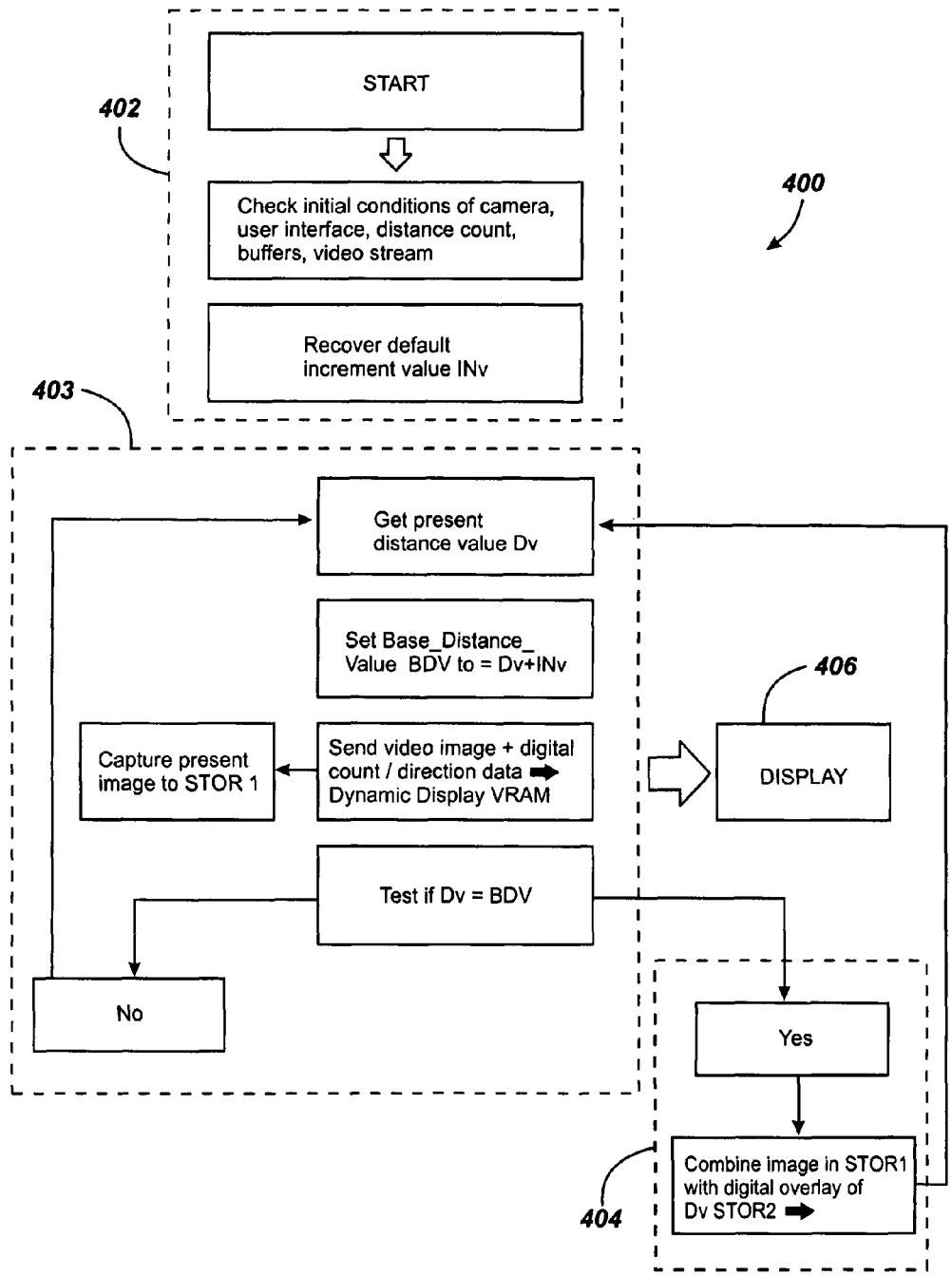
FIG. 4 is a flow diagram illustrating the manner in which the system of FIG. 1 processes the flow of several cable count and camera image data layers to form a composite stored image.

FIG. 4 illustrates a general logical flow 400 of the capture of in-pipe images at pre-defined increments of distance. In FIG. 4, an initialization stage 402 establishes basic conditions, and recovers a default increment value which may have been user-selected or left to the system default. A main program loop 403 establishes the starting value of the distance counter Dv, adds the desired increment INv to it, and continuously compares the distance counter's reported value with the result (BDV). The image from the camera FOV combined with digital distance/direction information is repeatedly sent to the display 406, and to storage as controlled by the UI assembly's firmware, and a test is performed to determine whether the present distance value (that is, the new value of Dv after updating) is equal to the BDv result. If the accrued Dv is equal to BDv, a subroutine 404 is activated causing the image with overlays showing the Dv value and direction of travel, to be copied from STOR1, the SD card, or from volatile memory, and written to STOR2, the USB thumb drive, for example.

User commands, such as those issued to capture an image of the camera FOV, may be facilitated by the optional keyboard, the user-interface keypad, or by the addition of other means such as foot-pedals, voice-activated microphone and voice recognition software, or other means.

In another embodiment of the present invention, the program controlled image captures may be stored in a time-tagged directory for the inspection job, defined by user initialization and customizable through the user interface, and subdivided in storage into directories according to a structure most convenient for the user and for the execution of the storage algorithms. For example, an inspection folder "2008_02_28-1" might contain subdirectories "/Autolog" for images captured every distance increment regardless of camera motion, "/Pause" for images captured when camera motion was below a certain threshold, if the distance counter had incremented some minimum distance from the last such image; and "/User" for images captured on user instruction such as by pressing a "Capture" button on the user-interface panel. Other hierarchies of image storage which prove useful and efficient may be used, as will be readily understood by persons skilled in the art of video pipe inspection.

Figure 5:
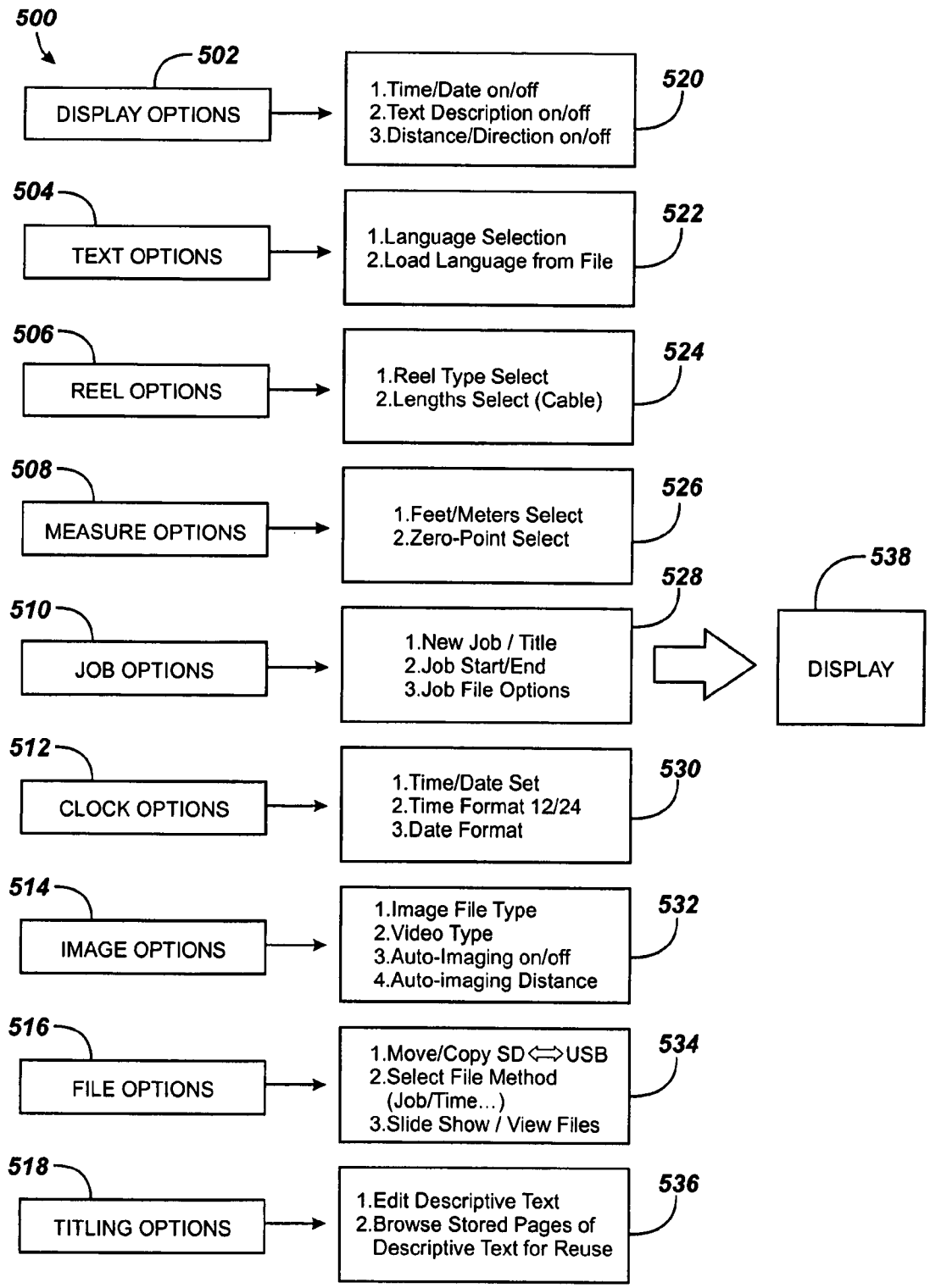
FIG. 5 illustrates an exemplary menu structure for the system of FIG. 1.

FIG. 5 illustrates a menu structure for organizing features and functions available to the user. In FIG. 5, a configuration of menu categories is shown on the left, which in one embodiment would be scrollable or otherwise selectable to enable the user to configure the system for local requirements and use its capabilities as needed. In FIG. 5, the primary menu 500 provides choices for configuring the display information 502 to include or exclude such information items as date and time, titling, and distance and direction 520 from the video display 538. A Text Options menu 504 enables the selection of display language, for example, English, French, etc. and the capability to upload a language file which would expand the menu 522 accordingly. The Reel Options menu 506 enables the user to configure the system for the reel model and cable length 524, he is using, which is necessary for refining the measurement of distance as a function of reel rotation. Measure Options 508 enable the user to display distant in metric or English units 526. Job Options 510 allow the creation of a new job, defining a job title such as "1234 Greenwood Avenue," for example, starting file-saving to a job directory, signal the end of a job 528, etc. Clock Options 512 allow for the setting of time and date, and defining the display and storage format of date-time tags 530. Image Options 514 enables the operator to define the file type for saved files, such as TIFF, JPEG, etc., define the video type for systems providing video capture, and set a preferred increment for distance 532 In the main menu 500, the File Options selection 516 provides sub-options 534 to move or copy files to the USB device, for example, select a method of file organization (job, time, etc.) and view files singly or as a slide show. In the main menu 500, the Titling Options selection 518 offers a sub-menu 536 including editing the titling text, storing and browsing saved titling pages, etc.

In another embodiment of the present invention, a method is provided for multiplexing data in the same channel as video signals by means of frequency-division multiplexing using the unidirectional video analog signal as a primary base band. To this signal a high frequency ASK (amplitude shift keying) signal is added at each end of the cable, providing bi-directional data communications. Specifically, in one embodiment, the video signal originates in a camera and occupies the frequency band of "DC" to approximately 5 MHz, and the data signal from camera resides on a 10.7 MHz ASK carrier, and data to camera resides on a 13.56 MHz ASK carrier.

The system of the present invention may consist of a number of nodes, such as, for example, the camera and the main processor in the present application. Data is extracted at each node and repeated through the local node processor. Thus, data may be daisy chained from one end to the other, with any number of nodes in between. Data is transmitted as an approximately 50% modulated ASK signal. This means that the carrier is always present (50% of maximum amplitude)

for a data "zero" and 100% amplitude for a data "one" bit. The push-cable may attenuate this signal by a large amount, but by using logarithmic amplification, the average value (RSSI or Received Signal Strength Indicator) is related to length of cable, and the relative relationship between data 0 and data 1 is approximately constant. The data is Manchester encoded. Manchester encoding provides simple encoding with no long period without a level transition. This helps clock recovery. Thus, data and clock can be easily extracted from the received bit stream. There is a unique pulse width for start and stop bits, so data can be sent in batches. This allows data to be sent and received by a very simple half-duplex processor without losing data in either direction due to collision. The transmitted and received data is FDM separated. Each data packet has a source and destination node, and message type (keep alive, query, response, autonomous) as well as the desired data. Data not intended for the "local node" is passed to the transmitter of the local node and thus relayed on to the next node.

Figure 6:
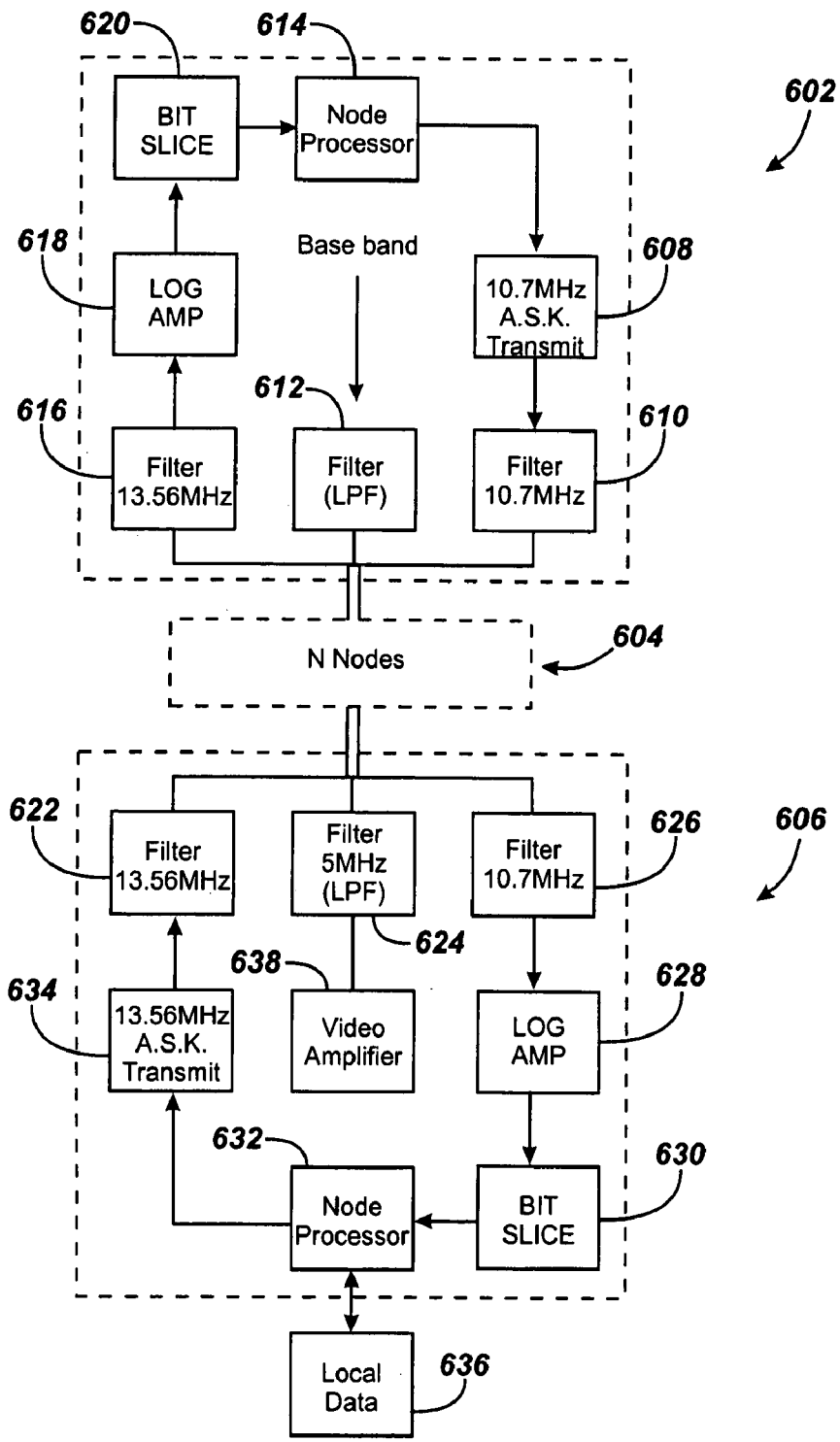
FIG. 6 is a block diagram of the data link of the system of FIG. 1.

Turning to FIG. 6, an illustration of the node-to-node relay scheme is provided. In FIG. 6, remote node 602 and a local node 606 are exchanging data through N intermediary nodes 604. In one implementation of the present invention, the remote node is a camera. The remote node processor 614 monitors base band video transmission through a low-pass filter (LPF) 612, and data transmission such as from sensors through a 10.7 MHz A.S.K. transmission algorithm 608 and filter 610. These transmissions may go through N number of other nodes 604 using essentially the same scheme as shown in local node 606. Incoming data passing through the 10.7 MHz filter 626 is passed to a logarithmic amplification routine 628, bit-sliced 630, and formatted and passed to the local node processor 632. Incoming (at the local node) 5 MHz LPF video is passed through a video amplifier 638 described in FIG. 7. Local data 636 such as command strings, for example, from the local node processor 632 are sent through 13.56 MHz A.S.K. encoding 634 and transmitted via a 13.56 MHz filter to a target node 602, filtered on receipt by a 13.56 MHz filter 616, amplified logarithmically 618, bit-sliced 620 and received by the remote node processor 614.

In addition to providing a data link, the system of the present invention is able to automatically correct for the current loss in the push-cable, thus greatly improving the quality of the video signal. Since there is always a data carrier, the RSSI (Received Signal Strength Indicator) can be used to infer the degree of video attenuation. Thus, by using the fact that the impedance of a diode varies with current through the diode, this signal can be used to alter the frequency response of a video amplifier. By using multiple diodes, and by altering the relative current in each diode, the frequency response of the amplifier can substantially correct the incoming video, restoring video quality image.

There are two primary compensation requirements: Different cable lengths may be used in different applications, imposing differing degrees of attenuation on the transmitted base band signal, and the present invention automatically addresses this aspect. In a cable, the attenuation and frequency response also change with ambient temperature. The present invention responds to the observed signal strength, which reflects attenuation in transmission, and the attenuation is automatically compensated for in the signal processing. The push-cable attenuation through the push-cable is frequency selective: the high frequencies are attenuated more than the lower frequencies, and thus one of the purposes of the disclosed correction mechanism is to provide a means of automatically adjusting the frequency response as well as attenuation.

Figure 7:
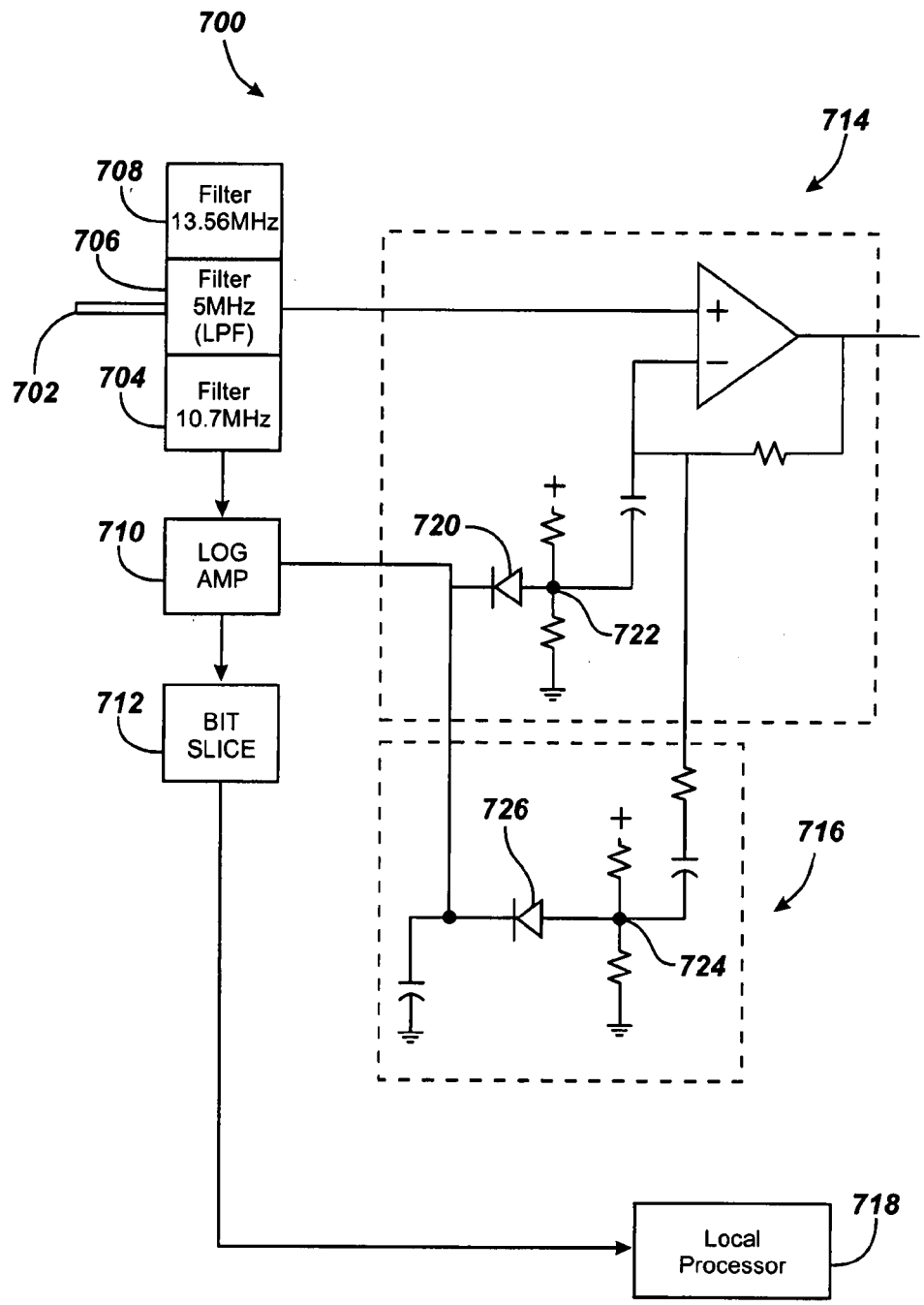
FIG. 7 is a schematic diagram illustrating the further details of the data link of FIG. 6.

Turning now to FIG. 7, these principles are illustrated in a data link circuit 700 representing a more detailed view of part of the data link of FIG. 6. In FIG. 7, LPF data 702 (video) is passed to a video amplifier 714. The frequency response of the video amplifier 714 is controlled by the impedance of diode 720. Received Signal Strength Indicator (RSSI) arriving via the 10.7 MHz filter 704 is measured at the logarithmic amplifier 710 and in combination with a selected threshold voltage 722, modulates the impedance of diode 720, which in turns modifies the amplification of the video amplifier 714. This compensates for any attenuation in video signals caused by longer cable length or by ambient temperature of the cable in use.

Similarly, a second identical sub-circuit 716 may be used to provide further compensation by selecting an appropriate value for threshold voltage 724 and modifying the impedance of diode 726. By using multiple diodes, and by defining the voltage for each threshold (threshold 722 and threshold 724 in FIG. 7), the frequency response of the amplifier can substantially perfectly correct the incoming video, restoring video quality image. Multiple iterations of this design may be added, for example, to expand the correction factor to offset attenuation at higher frequencies. This allows the system to compensate for differing cable-lengths in the unit, for example, and varying ambient temperature environments of operation, automatically.

In an alternate embodiment of the present invention, the determination of when to take and store images is determined by logic established in the field-programmable gate array (FPGA) unit in the UI assembly. In this embodiment, the FPGA continuously stores samples from defined sample regions in each field of each frame of video. When a signal from the processor based on time, distance, or some sensor input, is sent to the FPGA, the next full field is captured into dynamic RAM memory. A comparison routine identifies differences between Y samples of the present frame and the stored frame, and by evaluating the number of differences, the degree of relative motion of the camera is defined. If the difference is low enough, the DRAM-stored image is saved, for example as a JPEG formatted file. This embodiment allows the camera images to be saved only when the rate of motion is below a predetermined threshold level in order to ensure sufficient image quality for the pipe inspection job, avoiding the storage of images which are unusable due to motion blur. This method may run in an automated fashion independent of distance count, monitored only by relative change in the FOV as analyzed by the FPGA firmware. It may also be coordinated with distance count or with time increments selected by the user. The logic of comparison of NTSC frames (or their converted equivalent in a format such as YUV data) will be better implemented by dividing the pixel data of the subject frame into paxels (regions of a generally rectangular form) and comparing a paxel with its corresponding data from the preceding frame to determine the degree of change by subtraction. By using paxel-comparison, a situation such as running water within a pipe causing constant motion in one area of the frame would not be interpreted as camera movement and would not prevent the capture of images if the other paxels were indicating a state of no-motion. A paxel of high interest could be used by itself as a determinant to capture an image, for example, by using direct subtraction of the pixels within that paxel.

Under the paxel comparison scheme, a neural net architecture may be used as a generalized voting device to interpret the change indications of the various paxels at a given moment in time. Additionally, an adjustable threshold may be used such that depending on the setting of the threshold, fewer paxel indications would be required to signal that a picture should be saved. At a low threshold, a single paxel showing low motion results (in comparison with the preceding frame's values for the same paxel) would be sufficient to trigger image capturing, while at a high threshold a concurrence of from 2 . . . n paxels would be required to trigger the same action.

In a further embodiment of the present invention, output from the camera's video processor such as the DM355 from Texas Instruments is routed through a processing algorithm to identify changes in the motion of the camera, triggering automatic image capture when the camera is at rest, for example, or nearly so. In this embodiment, the H3A chip component in the DM355, or a similar auto-focus engine in comparable camera chips, is parsed to detect relative peaks and relative level periods in the auto-focus change rate. One method of doing this that has been successfully tested, for example, is to use a TVP 5150 chip to convert the NTSC feed from the camera head into YUV-encoded data streams which when fed to the camera processor produce easily detectable peaks and plains in the color-sum output streams indicative of relative motion of the camera. Thus the same mechanism being used by the camera to transmit video is innovatively used to analyze salient aspects of the environment for diagnostic purposes.

The motion of the camera head causes the output of the camera's auto-focus engine to produce erratic values, while a camera at rest produces more stable values from the autofocus engine. An algorithm that enables the detection of moments of substantially no-motion of the camera head may include the following steps:
1. Performing a high-pass filter in the spatial domain on the image data, or alternatively performing a first-difference derivative computation thereon;
2. Performing a time-domain high-pass filter on the time-series from the auto-focus engine,
3. Computing the value of the high-pass filters using RMS comparison, peak-to-peak values, variance or standard deviations; and
4. Signaling for an image to be captured when the variance drops below a pre-determined threshold value.

One optimized image capture algorithm is:
1. Capture Images at 4 frames per second (except):
2. If the camera is moving (per the AF engine or other image analysis) only capture low resolutions images, say JPEG quality setting 10.
3. If the camera stops (per the AF engine or other image analysis), immediately capture one (or a short series {perhaps 2-10 images} if frame stacking is utilized to improve resolution) higher resolution image, perhaps at a JPEG quality setting 80.
   a. Either stop capturing new images or reduce the frame rate to avoid oversampling the same, unchanging image if the camera remains stopped.
   b. If the drum counter is stopped for a period of time, either stop acquiring new images or capture new images at a very low rate, perhaps at lower resolution.

In yet another embodiment of the present invention, the camera chip's white-balance engine may similarly be used to detect transitions between cast-iron, PVC or ABS piping, using a similar algorithm adapted to the white-balance engine in the camera chip set.

In still another embodiment of the present invention, the same principles may be applied using the auto-exposure engine of the camera chip set to identify points in time when side branches in the main pipe are encountered, due to their appearance to the camera as low-reflectivity holes. In use, for example, the cable-counter's distance data at such a point may be latched, triggered by a relatively sudden color transition, and stored with average color data from before and after the transition; the latched cable count data would thus enable an inspector to return to the point where the transition was detected for closer inspection. As may be readily grasped by one skilled in the art, the principle of paxel-comparison described earlier may be applied to the data from the auto-exposure, white-balance, or auto-focus engines in a similar method to the image data comparison described.

Figure 8:
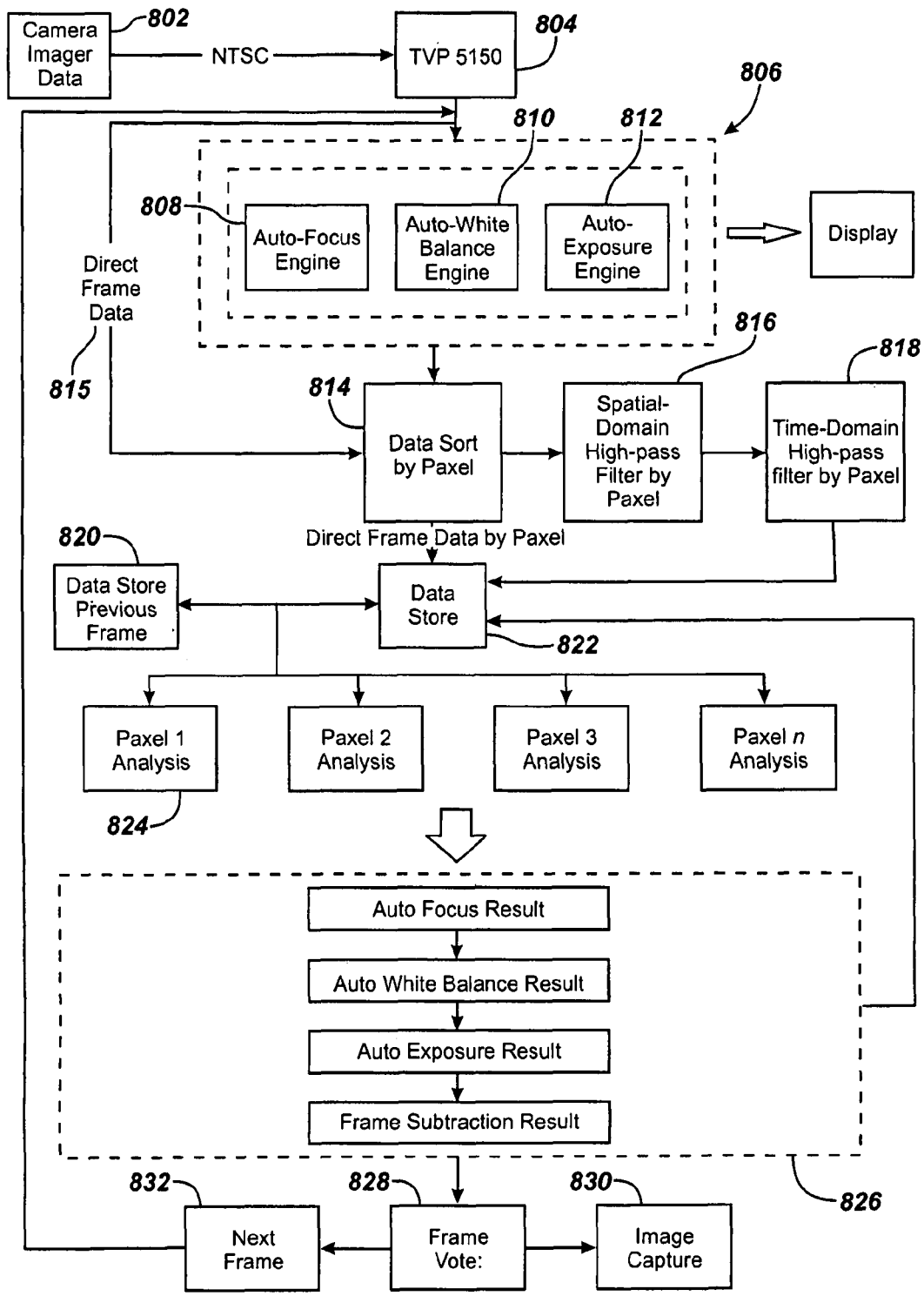
FIG. 8 is a flow-diagram illustrating of the detection of motion or the absence of motion of the camera head of the system of FIG. 1 during a pipe inspection based on electronic data from the camera chip set and the use of detected motion to trigger the generation of an image of the interior of the pipe being inspected.

FIG. 8 illustrates the sequence of steps and conditions involved in the use of camera chip set data streams as a means of detecting motion thresholds and thus triggering the capture of images only during periods of relatively little camera motion. In FIG. 8, inputs from camera imager 802 in NTSC format are passed in this example to a TVP5150 chip 804 and output in YUV format. In this embodiment the conversion is from NTSC to YUV data; other conversions may be found to be advantageous. Other formats may be used and may require alternative chip sets.

Converted data is then subdivided into data from the several subsystems in the H3A module to a separation routine to identify data from the Auto-focus 808, Auto-White Balance 810, and Auto-Exposure engines 812 within the module. Data is further divided 814 by paxel region. For each paxel region, a spatial-domain high pass filter 816 is applied, and for each paxel a time-domain high pass filter 818 is applied, and the data from both processes stored 822. Data 820 stored from the next-earlier frame is available for comparison. In addition to the H3A module data sets 808, 810, 812, a direct comparison of frame video data 815 may also be done by simple subtraction of values. These comparisons are similarly subject to sorting by paxel region.

An analysis routine 824 is done for each paxel's data. The number of paxels into which the total set of pixels is divided is a function of the application and the particular system components used. The use of one or another set of data—white balance, auto focus, auto-exposure or direct frame subtraction—is also dependent on the particular application to which the present invention is put. In FIG. 8 results 826 are produced for all four data sets for purposes of illustration.

These results 826 are passed to a "voting" routine 828 to determine a net decision as to the motion threshold between the present frame and the frame just prior. The decision may be based on any one, or a combination, of the data analyzed. For example, a positive decision to capture an image may be based on the auto-exposure values for a paxel of interest changing indicating a sudden brightness transition as from an ABS or cast iron pipe to a PVC pipe. Motion detection indicated by variation in auto-focus values may prompt an image save in one paxel of interest but not in another (for example, where water running through the bottom of a pipe produces constant motion, the lower image paxels would be discounted). Frame subtraction values for paxels of interest may be relied on in an application where processing resources are constrained. Auto-exposure values may trigger an image capture with distance value from a cable counter to indicate a low-reflectivity gap indicative of a side-branch entering the pipe. Other applications of the results data 826 may be configured for other application-specific approaches.

A positive decision results in the image values from the present frame being stored 830 or captured as part of the inspection record; otherwise, the next frame 832 is converted and analyzed. In an alternative embodiment, conversion and storage may be timed independently of image capture decision processing if firmware and hardware capacity supports it.

In yet another embodiment of the present invention, a variable-rate file encoding scheme may be used. The detected conditions (as sensed by the camera mechanisms described above or by other sensors on board the camera) can be encoded into the captured images allowing the individual frames to be played back for different pre-determined amounts of time, on an image-by-image basis, depending, for example, on whether the image was taken while the camera head was in motion, take upon detection of a pipe transition, captured during a short motion stoppage, captured during a long motion stoppage, and so forth. Certain file protocols including the MJPEG protocols allow individual frames to have variable playback rates encoded with them. The encoding scheme can be related to playback to reduce viewer time required to examine images containing less relevant information, such as motion-blurred images, and provide more playback time for images containing more relevant information, such as a stopped, high-resolution image. An example of playback times under this embodiment is illustrated in Table 1 set forth hereafter.

TABLE 1

Variable-Rate Playback Times

| Image | Playback period | Conditions |
| --- | --- | --- |
| Image 1 | 250 ms/4 frames per second | Camera moving |
| Image 2 | 250 ms | Camera moving |
| Image 3 | 2 seconds | Camera stopped. High-resolution image. |
| Image 4 | 250 ms | Camera moving again. |
| ... | | |
| ... | | |
| Image 62 | 30 seconds | Camera stopped for a longer period of time. |

The present invention can advantageously use variable rate motion jpeg video (MJPEG-AVI) file encoding. This allows the pipe inspection to display the high resolution images at a relatively slow rate and the low resolution images at a relatively high frame rate. An MPEG file is a video format file that comprises a plurality of jpeg encoded still images that are attached to one another in such a manner that when they are displayed in sequence, at a particular interval (frame rate), they represent a motion video. To make an MPEG file playable in a standard personal computer media viewer, it must be placed in a container that coordinates the changing of images and the synchronization of audio. One way a container coordinates the playback of an image sequence is by providing a table of indices which the player advances through at a periodic rate (the frame rate), displaying each image as it is referenced by the index. A variable frame rate effect can be achieved by duplicating frames so that the same frame is displayed multiple times. In the case of a container that has this type of index table, the file size may be greatly reduced by updating the index table such that multiple indices reference the same image data, rather than needing to duplicate the image data itself The "AVI" container is one common example of a file format that operates in this fashion.

Audio frames may be handled the same way. A separate audio table can control the playback sequence for audio frames so that they may be synchronized with corresponding image files. If audio frames can be made to repeat (for instance, in the case of silence), one audio frame may be referenced multiple times in the table to further conserve file size. The index tables can be manipulated to allow sub-1 frame per second playback rates. A container will typically only allow integer numbers for the frame rate specification. If it is desirable to have less than one frame per second (i.e. multiple seconds per frame), this may be done by duplicating each frame such that the frame rate specified in the file is some integer multiple of the effective frame rate.

A representative sequence of steps would be:
1.) Start a new AVI file
2.) Acquire a new image or an audio frame
3.) Decide if the frame has interesting data
   a. For an image, this decision may be made by finding out if this image is substantially different than the last one, or if it contains an image that is sharp beyond some threshold.
   b. For an audio frame, this may be whether or not the audio is muted.
4.) If the data is interesting, record the data in the AVI file and make the next entry in the index table point to the new data.
5.) If the data was not interesting, record a pointer to the default frame in the index table.
   a. For audio, this will be a frame that contains no audio data (silence).
   b. For an image, this will be the most recent image recorded.
6.) Repeat the process until the user signals to stop recording.
7.) Close the file.

Figure 9:
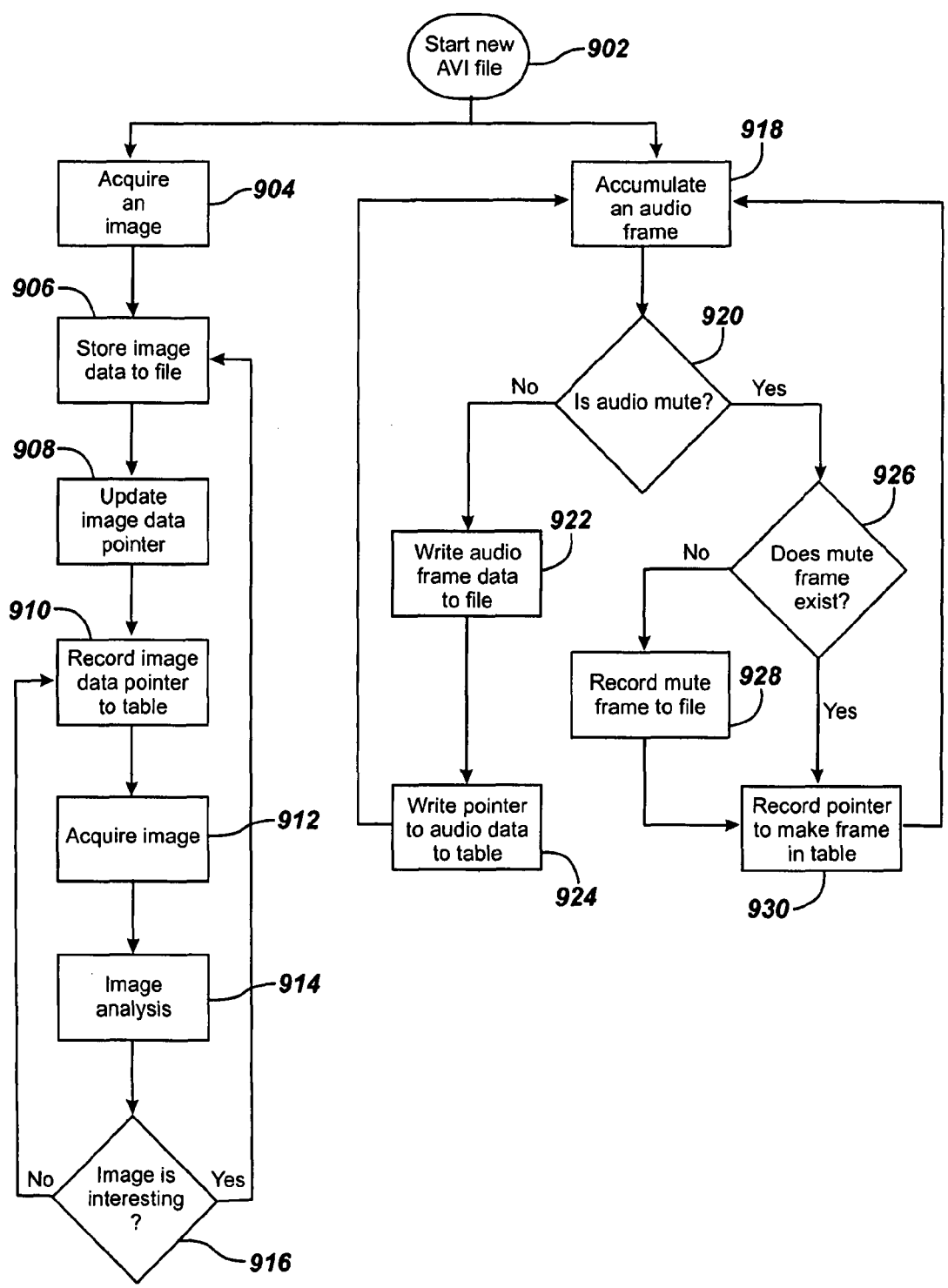
FIG. 9 is a flow chart illustrating steps of a method of variable-timed image playback.

FIG. 9 is a flow chart that illustrates a sequence of steps for managing image frames or audio frames as described above. A new AVI file is created in step 902 into which an image is acquired in step 904. Image data is stored to a file in step 906 and the image data pointer is updated in step 908. An image data pointer is recorded to a memory table in step 910. The image is acquired in step 912 by a processing algorithm which analyzes the image in step 914 and decides whether the image is of interest in step 916. If so, the image is stored to a file in step 906 and tagged as being of interest with its data appropriately modified. If it is not, a pointer to the image data is recorded.

Referring to FIG. 9, the audio content of an individual frame is accumulated in step 918 and the state of audio is checked as mute or not-mute in step 920. If the audio is mute a determination is made in step 926 whether a mute frame exists. If so, a pointer is recorded in step 928. If no mute frame exists, a pointer is recorded in step 930 to the mute frame which may be played repeatedly as needed. If the audio is not mute in step 920, the audio frame data is written to a file in step 922 and a pointer to it is written to the pointer table in step 924. The next frame's audio is then processed.

Figure 10:
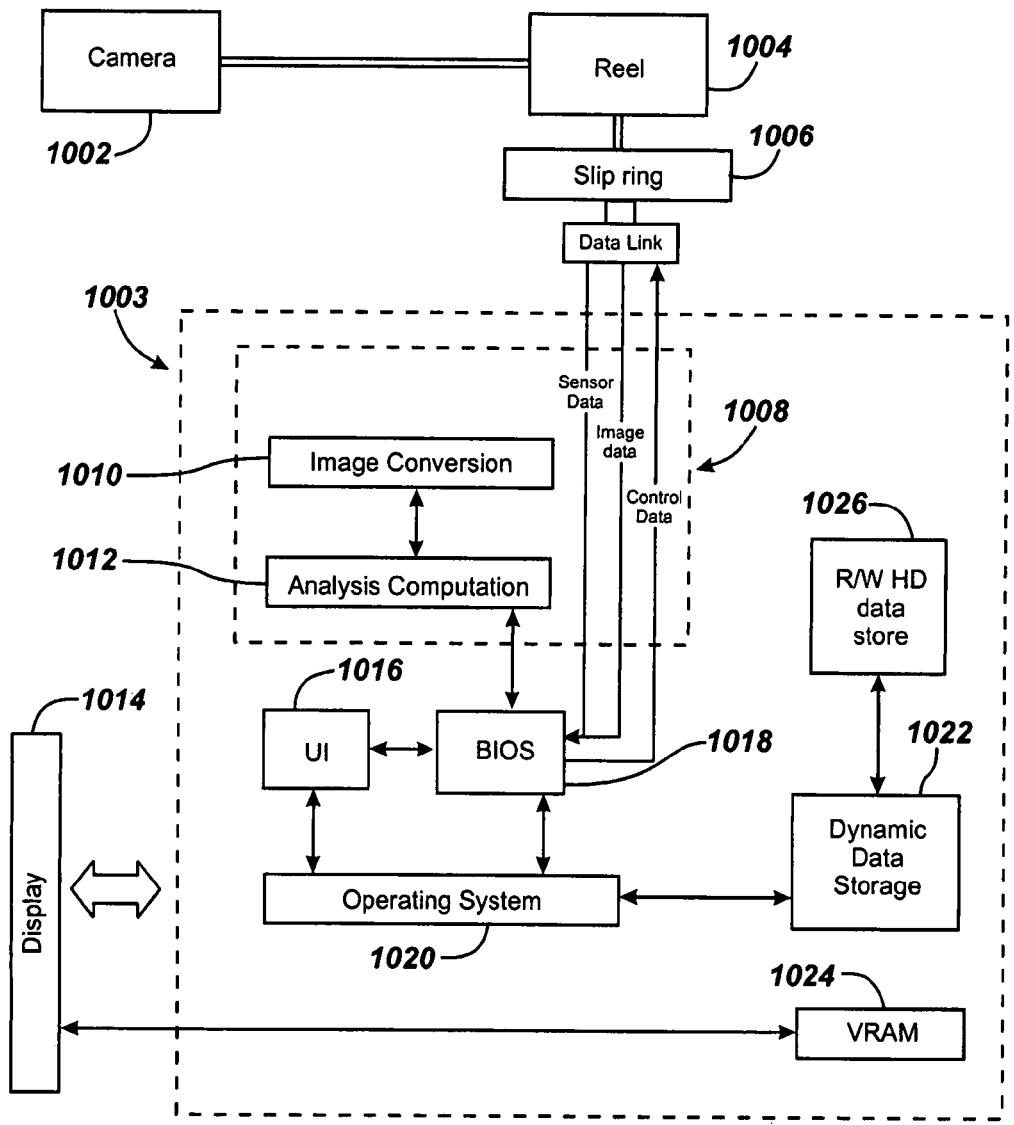
FIG. 10 is a block diagram of a pipe inspection system capable of variable-timed image playback.

Referring to FIG. 10 an analog camera 1002 provides NTSC data and other applicable sensor data transmitted along conductors embedded in the inspection push-cable to the push-cable reel 1004. The data is transmitted via a slip-ring mechanism 1006 to a camera control (CCU) block 1003. Within the CCU 1003 a processing unit 1008 includes hardware and firmware/software elements 1010 for image conversion and a memory 1012 for data analysis and computation. A BIOS subsystem 1018 controls data transfers among system blocks under the general control of a high-level architecture and operating system 1020. Under firmware/software control data is stored in a dynamic RAM 1022 and display data is transferred to Video RAM 1024 when due for display on the system display 1014. Data may be written to and read from permanent memory storage 1026 which may be a hard disk, removable media, or similar hardware device.

Clearly, other embodiments and modifications of this invention may occur readily to those skilled in the art in view of these teachings. Therefore, this invention is to be limited only by the following claims, which include all such embodiments and modifications when viewed in conjunction with the above specification and accompanying drawing.

We claim:

1. A pipe inspection imaging system, comprising:
   a push-cable;
   a camera head operatively connected to a distal end of the push-cable, the camera head including an image sensor capable of generating images of an interior of a pipe in which the camera head is inserted; and
   processing circuitry connected to the image sensor and configured to enable images to be automatically captured at predetermined distances traveled by the camera head within the pipe.

2. The system of claim 1 and further comprising:
   a reel for paying out the push-cable; and
   a slip-ring assembly for providing signals representing distance information during a pipe inspection.

3. The system of claim 1 wherein the processing circuitry combines the distance information with a plurality of video images generated by the image sensor in a time-synchronized manner.

4. The system of claim 3, wherein the processing circuitry includes:
   a data transmission circuit that transmits data between a plurality of nodes at a frequency that does not substantially interfere with a normal base band video transmission frequency; and
   a circuit that receives the video images and corrects for attenuation based on signal strength.

5. The system of claim 4 further comprising:
   processing circuitry for combining ASK (Amplitude Shift Keying) encoding, logarithmic amplification, data slicing, Manchester encoding, and start and stop widths to transmit data from the camera head to a local node processor; and
   processing circuitry for automatically compensating for attenuation caused by signal frequency, cable length or ambient temperature of the push-cable and rectifying the effect of such attenuation on the video fidelity.

6. The pipe inspection system of claim 1 further including a user interface configured to receive a user selected image capture distance value and configure the camera head to capture images at the image capture distance value.

7. A pipe inspection imaging system, comprising:
   a push-cable;
   a camera head operatively connected to a distal end of the push-cable, the camera head including an image sensor capable of generating images of an interior of a pipe in which the camera head is inserted; and
   processing circuitry connected to the image sensor and configured to enable images to be automatically captured at predetermined time intervals as the camera head travels within the pipe if the images are substantially in focus.

8. A pipe inspection imaging system, comprising:
   a push-cable;
   a camera head operatively connected to a distal end of the push-cable, the camera head including an image sensor capable of generating images of an interior of a pipe in which the camera head is inserted; and
   processing circuitry connected to the image sensor and configured to enable images to be automatically captured upon detecting that the camera head has substantially stopped moving within the pipe.

9. The pipe inspection system of claim 8 wherein the processing circuit is configured to detect relative lack of motion of the camera head based on an analysis of signals output from a portion of the processing circuitry selected from the group consisting of auto-exposure, white-balance and auto-focus engines.

10. The pipe inspection system of claim 8 wherein the images that are automatically captured upon detecting that the camera head has substantially stopped moving within the pipe are provided at a first resolution and wherein the processing circuitry is further configured to provide a second set of images, at a resolution lower than the first resolution, when the camera head is moving.

11. A pipe inspection imaging system, comprising:
    a push-cable;
    a camera head operatively connected to a distal end of the push-cable, the camera head including an image sensor capable of generating images of an interior of a pipe in which the camera head is inserted; and
    processing circuitry connected to the image sensor and configured to enable images to be automatically captured at predetermined intervals determined by at least two criteria selected from the group consisting of time, distance, image sharpness and camera head motion.

12. A pipe inspection imaging system, comprising:
    a push-cable;
    a camera head operatively connected to a distal end of the push-'cable, the camera head including an image sensor capable of generating images of an interior of a pipe in which the camera head is inserted; and
    processing circuitry connected to the image sensor and configured to enable images to be automatically captured at predetermined image compression levels based on a degree of detected motion of the camera head within the pipe.

13. A pipe inspection imaging system, comprising:
    a push-cable;
    a camera head operatively connected to a distal end of the push-cable, the camera head including an image sensor capable of generating images of an interior of a pipe in which the camera head is inserted; and
    processing circuitry connected to the image sensor and configured to enable images to be stored with zonal based data selected from the group consisting of auto-focus data, auto-exposure data and auto-white balance data.

14. The system of claim 13 wherein the processing circuitry automatically captures images based on the zonal based data.

15. A pipe inspection imaging system, comprising:
    a push-cable;
    a camera head operatively connected to a distal end of the push cable, the camera head including an image sensor capable of generating images of an interior of a pipe in which the camera head is inserted; and
    processing circuitry connected to the image sensor and configured to enable images to be digitally compressed at a predetermined relatively slow frame rate and for synchronizing a digitally compressed audio channel with the compressed images.

16. A pipe inspection imaging system, comprising:
    a push-cable;
    a camera head operatively connected to a distal end of the push-cable, the camera head including an image sensor capable of generating images of an interior of a pipe in which the camera head is inserted; and processing circuitry connected to the image sensor and configured to enable images to be captured in an automatic mode at predetermined intervals as the camera head travels within the pipe or in an override mode initiated by operator command.

17. A pipe inspection imaging system, comprising:
a push-cable;
a camera head operatively connected to a distal end of the push-cable, the camera head including an image sensor capable of generating images of an interior of a pipe in which the camera head is inserted;
processing circuitry connected to the image sensor including a data transmission circuit that transmits data between a plurality of nodes at a frequency that does not substantially interfere with a normal base band video transmission frequency; and
a circuit that receives the video images and corrects for attenuation based on signal strength.

18. A pipe inspection imaging system, comprising:
a camera head operatively connected to a distal end of the push-cable, the camera head including an image sensor capable of generating images of an interior of a pipe in which the camera head is inserted; and
processing circuitry connected to the image sensor including means for combining ASK Amplitude Shift Key) encoding, logarithmic amplification, data slicing, Manchester encoding, and start and stop widths to transmit data from the camera head to a local node processor.

19. A pipe inspection imaging system, comprising:
a push-cable;
a camera head operatively connected to a distal end of the push-cable, the camera head including an image sensor capable of generating images of an interior of a pipe in which the camera head is inserted; and
processing circuitry connected to the image sensor and configured to enable images to be automatically captured at a relatively low resolution when the camera head in moving in the pipe and at a relatively high resolution when the camera head is stopped within the pipe as indicated by processing signals from a camera engine in the camera head, the camera engine being selected from the group consisting of an auto-focus engine, an auto-exposure engine, and an auto-white balance engine.

20. A pipe inspection imaging system, comprising:
a push-cable;
a camera head operatively connected to a distal end of the push-cable, the camera head including an image sensor capable of generating images of an interior of a pipe in which the camera head is inserted; and
processing circuitry connected to the image sensor and configured to enable images to be automatically captured at different resolutions depending on an optically detected state of motion of the camera head within the pipe.

21. The system of claim 20 wherein the images are captured at predetermined time intervals.

22. The system of claim 20 wherein the images are captured at predetermined distances of insertion of the camera head within the pipe.

23. The system of claim 20 wherein the state of motion of the camera head is detected based upon signals from a camera engine in the camera head, the camera engine being selected from the group consisting of an auto-focus engine, an auto-exposure engine, and an auto-white balance engine.

24. A pipe inspection imaging system, comprising:
a push-cable;
a camera head operatively connected to a distal end of the push-cable, the camera head including an image sensor capable of generating images of an interior of a pipe in which the camera head is inserted; and
processing circuitry connected to the image sensor and configured to automatically capture a first larger set of images when the camera head is moving within the pipe and a substantially smaller second set of images when motion of the camera head has stopped, and generate a pseudo-video file utilizing variable frame rate motion jpeg processing so that when stored and later viewed the pseudo-video file appears to display the interior of the pipe in real time as the camera head moves within the pipe, with images in the second set being re-played instead of storing multiple identical images in order to substantially reduce the size of the pseudo-video file.

25. A pipe inspection system, comprising:
a camera head including an image sensor;
a push cable coupled to the camera head for urging the camera head along an interior of a pipe under inspection;
a processor for producing a GUI image data signal representing conditions in the pipe under inspection;
a display connected to the processor for displaying to an operator, at a predetermined video resolution, a GUI image based on the GUI image signal; and
a control that provides a user with automatically captured images from a pipe inspection at user-selected increments of distance, with overlays incorporated into the images displaying predetermined distance and/or direction information.

26. The pipe inspection system of claim 25, wherein the system further includes an interface to receive an input comment from a user and add the comment to one or more of the captured images.

27. The pipe inspection system of claim 25, wherein the system further includes an a clock circuit to generate a date associated with the images, wherein the date is stamped to one or more of the captured images.

28. The pipe inspection system of claim 25, wherein the system further includes an interface to receive an input selection of an overlay from a user and incorporate the user-selected overlay with one or more of the captured images.

* * * * *